United States Patent
Achilefu et al.

(10) Patent No.: US 7,510,700 B2
(45) Date of Patent: Mar. 31, 2009

(54) PATHOLOGICAL TISSUE DETECTION AND TREATMENT EMPLOYING TARGETED BENZOINDOLE OPTICAL AGENTS

(75) Inventors: Samuel Achilefu, St. Louis, MO (US); Richard B. Dorshow, St. Louis, MO (US); Raghavan Rajagopalan, Woodmere Village, OH (US); Joseph B. Bugaj, St. Charles, MO (US)

(73) Assignee: Mallinckrodt Inc, Hazelwood, MO (US)

( * ) Notice: Subject to any disclaimer, the term of this patent is extended or adjusted under 35 U.S.C. 154(b) by 191 days.

(21) Appl. No.: 11/388,382

(22) Filed: Mar. 24, 2006

(65) Prior Publication Data

US 2007/0128115 A1 Jun. 7, 2007

Related U.S. Application Data

(63) Continuation of application No. 10/847,257, filed on May 17, 2004, now Pat. No. 7,201,892, which is a continuation of application No. 10/847,256, filed on May 17, 2004, now Pat. No. 7,252,815, which is a continuation of application No. 10/847,121, filed on May 17, 2004, now Pat. No. 7,128,896, which is a continuation of application No. 09/978,725, filed on Oct. 17, 2001, now Pat. No. 6,761,878, which is a continuation of application No. 09/981,206, filed on Oct. 17, 2001, now abandoned.

(51) Int. Cl.
*A61B 10/00* (2006.01)
*A61B 5/00* (2006.01)
*A61B 8/00* (2006.01)

(52) U.S. Cl. .................. 424/9.6; 424/1.11; 424/1.65; 424/9.1; 424/1.69; 424/1.73; 424/1.49; 548/400

(58) Field of Classification Search ............... 424/1.11, 424/1.37, 1.49, 1.65, 1.69, 1.81, 1.85, 1.89, 424/9.1, 9.6, 1.73, 9.3, 9.4, 9.5, 9.7, 9.8; 534/7, 10–16; 548/100, 400; 530/300, 350, 530/387.1, 387.2, 322, 399; 514/285, 263.4, 514/390, 656, 654

See application file for complete search history.

(56) References Cited

U.S. PATENT DOCUMENTS

| 5,453,505 | A | 9/1995 | Lee et al. |
| 5,527,914 | A | 6/1996 | Hioki et al. |
| 5,665,328 | A | 9/1997 | Horan et al. |
| 5,672,332 | A | 9/1997 | Fung et al. |
| 6,180,087 | B1 | 1/2001 | Achilefu et al. |
| 6,183,726 | B1 | 2/2001 | Achilefu et al. |
| 6,258,340 | B1 | 7/2001 | Licha et al. |
| 6,395,257 | B1 | 5/2002 | Achilefu et al. |
| 6,506,539 | B2 | 1/2003 | Shinichi et al. |
| 6,761,878 | B2 * | 7/2004 | Achilefu et al. ............ 424/9.6 |
| 7,128,896 | B2 * | 10/2006 | Achilefu et al. ............ 424/9.6 |
| 7,201,892 | B2 * | 4/2007 | Achilefu et al. ............ 424/9.6 |
| 7,252,815 | B2 * | 8/2007 | Achilefu et al. ............ 424/9.6 |
| 7,431,925 | B2 * | 10/2008 | Rajagopalan et al. ..... 424/131.1 |
| 2002/0025491 | A1 | 2/2002 | Shinichi et al. |
| 2002/0044909 | A1 | 4/2002 | Achilefu et al. |
| 2003/0185756 | A1 | 10/2003 | Achilefu et al. |

FOREIGN PATENT DOCUMENTS

| EP | 0488511 | 6/1992 |
| EP | 0568022 | 11/1993 |
| EP | 0779540 | 6/1997 |
| EP | 0800831 | 10/1997 |
| EP | 0911693 | 4/1999 |
| JP | 2000/035647 | 2/2000 |
| WO | WO 98/22146 | 5/1998 |
| WO | WO 98/48838 | 11/1998 |
| WO | WO 98/48846 | 11/1998 |
| WO | WO 02/12398 | 2/2002 |
| WO | WO 02/32285 | 4/2002 |

OTHER PUBLICATIONS

Achilefu et al., Novel Receptor-Targeted Fluorescent Contrast Agents for In Vivo Tumor Imaging, 2000, Investigative Radiology, 35 (8), pp. 479-485.
Ballou et al., Tumor labeling in vivo using cyanine-conjugated monoclonal antibodies, 1995, Cancer Immunology, Immunotherapy, 41, pp. 257-263.
Ballou et al., Tumor Detection and Visualization Using Cyanine Fluorochrome-Labeled Antibodies, 1997, Biotechnology Progress, 13, pp. 649-658.
Bellinier et al., Murine pharmacokinetics and antiumor efficacy of the photodynamic sensitizer 2-[ 1-hexyloxyethyl]-2-devinyl pyropheophorbide-a, 1993, Journal of Photochemistry and Photobiology B: Biology, 20, pp. 55-61.
Benaron and Stevenson, Optical Time-of-Flight and Absorbance Imaging Biologic Media, Mar. 1993, Science, New Series, 259 (5100), pp. 1463-1466.
Caesar et al., The Use of Indocyanine Green in the Measurement of Hepatic Blood Flow and as a Test of Hepatic Function, 1961, Clinical Science, 21, pp. 43-57.
De Jong et al., Comparison of $^{111}$In-labeled Somatostatin Analogues for Tumor Scintigraphy and Radionuclide Therapy, Feb. 1998, Cancer Research, 58, pp. 437-441.
Dougherty et al., Photoradiation Therapy. II. Cure of Animal Tumors With Hematoporphyrin and Light, Jul. 1975, Journal of the National Cancer Institute, 55 (1), pp. 115-121.
Fantini et al., Assessment of the size, position, and optical properties of breast tumors in vivo by noninvasive optical methods, Apr. 1998, Applied Optics, 37 (10), pp. 1982-1989.

(Continued)

*Primary Examiner*—D. L Jones (57) ABSTRACT

Novel tumor specific phototherapeutic and photodiagnostic agents are disclosed. The compounds consist of a carbocyanine dye for visualization, photosensitizer for photodynamic treatment, and tumor receptor-avid peptide for site-specific delivery of the probe and phototoxic agent to diseased tissues. A combination of these elements takes full advantage of the unique and efficient properties of each component for an effective patient care management.

11 Claims, 5 Drawing Sheets

OTHER PUBLICATIONS

Folli et al., Immunophotodiagnosis of colon carcinomas in patients injected with fluoresceinated chimeric antibodies against carcinoembryonic antigen, Sep. 1993, Proceedings of the National Academy of Sciences USA, 89, pp. 7973-7977.

Frinking et al., Ultrasound Contrast Imaging: Current and New Potential Methods, 2000, Ultrasound in Medicine and Biology, 26 (6), pp. 965-975.

He et al., Measurement of blood volume using indocyanine green measured with pulse-spectrophotometry: Its reproducibility and reliability, 1998, Critical Care Medicine, 26(8), pp. 1446-1451.

Licha et al., New Contrast Agents for Optical Imaging: Acid-Cleavable Conjugates of Cyanine Dyes with Biomolecules, Jan. 1999, Part of the SPIE conference on Molecular Imaging: Reporters, Dyes, Markers, and Instrumentation, San Jose, Californis, 3600, pp. 29-35.

Mizuschige et al., Enhancement of Ultrasound-Accelerated Thrombolysis by Echo Contrast Agents: Dependence on Microbubble Structure, 199, Ultrasound in Medicine and Biology, 25 (9), pp. 1431-1437, date not available.

Mujumdar et al., Cyanine Dye Labeling Reagents: Sulfoindocyanine Succinimidyl Esters, 1993, Bioconjugate Chemistry, 4 (2), pp. 105-111.

Müller et al., Medical Optical Tomography: Functional Imaging and Monitoring, 1993, The Society of Photo-optical Instrumentation Engineers, vol. IS11, pp. 1-27.

Pelegrin et al., Photoimmunodiagnosis with antibody-flurescein conjugates: in vitro and in vivo preclinical studies, 1992, J Cell Pharmacology, 3, pp. 141-145.

Reynolds et al., Imaging of Spontaneous Canine Mammary Tumors Using Fluorescent Contrast Agents, 1999, Photochemistry and Photobiology, 70 (1), pp. 87-94.

Rezzoug et al., In vivo photodynamic therapy with meso-tetra(m-dydroxyphenyl)chlorine (mTHPC): influence of light intensity and optimization of photodynamic efficiency, Sep. 1996, The Society of Photo-Optical Instrumentation Engineers, 2924, pp. 181-186.

Sackman, Fluorescence Diagnosis in GI Endoscopy, 2000, Endoscopy, 32 (12), pp. 977-985.

Sandler et al., Organic Functional Group Preparations, 1986, Chapter 14/Azo Compounds, pp. 353-413.

Uwe Schobel et al.l, new donor-acceptor pair for fluorescent immunoassays by energy transfer, 1999, Bioconjugate Chemistry, 10, pp. 1107-1114 XP002346915.

Stranadko et al, Photodynamic therapy of recurrent cancer of oral cavity, an alternative to conventional treatment, Sep. 1996, The Society of Photo-Optical Instrumentation Engineers, 2924, pp. 292-297.

Taijeri et al., Fluorescent diagnosis of experimental gastric cancer using a tumor-localizing photosensitizer, 1997, Cancer Letters, 111, pp. 215-220.

Tearney et al., In Vivo Endoscopic Optical Biopsy with Optical Coherence Tomography, Jun. 1997, Science 276, pp. 2037-2039.

Tromberg et al., Non-invasive measurement of breast tissue optical properties using frequency-domain photon migration, 1997, Philosphical Transactions: Biological Sciences, 352 (1354), pp. 661-668.

Wagnieres et al., In Vivo Fluorescence Spectroscopy and Imaging for Onoclogical Applications, 1998, Photochemistry and Photobiology, 68 (5), pp. 603-632.

Weissleder et al., In vivo imaging of tumors with protease-activiated near-infrared fluorescent probes, Apr. 1999, Nature Biotechnology, 17, pp. 375-378.

Wilson et al., Optical Properties of Tissues, 1991, Encyclopedia of Human Biology, 5, pp. 587-597.

Woolam et al., Cancer Statistics, 2000: A Benchmark for the New Century, 2000, CA-A Cancer Journal For Clinicians, 50 (1), pp. 6-33.

* cited by examiner

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Phe. Artificial
      sequence is completely synthesized.
<220> FEATURE:
<223> OTHER INFORMATION: Xaa at locations 2 and 7 represents Cys with an
      intramolecular disulfide bond between two Cys
      amino acids.  Artificial sequence is completely synthesized.
<220> FEATURE:
<223> OTHER INFORMATION: Xaa at location 4 represents D-Trp. Artificial
      sequence is completely synthesized.

<400> SEQUENCE: 1

Xaa Xaa Tyr Xaa Lys Thr Xaa Thr
 1               5

<210> SEQ ID NO 2
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Phe. Artificial
```

-continued

```
       sequence is completely synthesized.
<223> OTHER INFORMATION: Xaa at locations 2 and 7 represents Cys with an
       intramolecular disulfide bond between two Cys
       amino acids.  Artificial sequence is completely synthesized.
<220> FEATURE:
<223> OTHER INFORMATION: Xaa at location 4 represents D-Trp.  Artificial
       sequence is completely synthesized.
<220> FEATURE:
<223> OTHER INFORMATION: Xaa at location 8 represents Thr-OH. Artificial
       sequence is completely synthesized.

<400> SEQUENCE: 2

Xaa Xaa Tyr Xaa Lys Thr Xaa Xaa
 1               5

<210> SEQ ID NO 3
<211> LENGTH: 11
<212> TYPE: PRT
<213> ORGANISM: Unknown
<220> FEATURE:
<221> NAME/KEY: MOD RES
<222> LOCATION: (1)...(11)
<223> OTHER INFORMATION: Bombesin analog

<400> SEQUENCE: 3

Gly Ser Gly Gln Trp Ala Val Gly His Leu Met
 1               5                   10

<210> SEQ ID NO 4
<211> LENGTH: 11
<212> TYPE: PRT
<213> ORGANISM: Unknown
<220> FEATURE:
<221> NAME/KEY: MOD RES
<222> LOCATION: (1)...(11)
<223> OTHER INFORMATION: Bombesin analog

<400> SEQUENCE: 4

Gly Asp Gly Gln Trp Ala Val Gly His Leu Met
 1               5                   10

<210> SEQ ID NO 5
<211> LENGTH: 8
<212> TYPE: PRT
<213> ORGANISM: Unknown
<220> FEATURE:
<221> NAME/KEY: MOD RES
<222> LOCATION: (1)...(8)
<223> OTHER INFORMATION: Cholecystokinin octapeptide analogs

<400> SEQUENCE: 5

Asp Tyr Met Gly Trp Met Asp Phe
 1               5

<210> SEQ ID NO 6
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at locations 3 and 6 represents Norleucine.
       Artificial sequence is completely synthesized.

<400> SEQUENCE: 6

Asp Tyr Xaa Gly Trp Xaa Asp Phe
     1               5

<210> SEQ ID NO 7
```

```
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Asp.  Artificial
      sequence is completely synthesized.
<220> FEATURE:
<223> OTHER INFORMATION: Xaa at locations 3 and 6 represents Norleucine.
      Artificial sequence is completely synthesized.

<400> SEQUENCE: 7

Xaa Tyr Xaa Gly Trp Xaa Asp Phe
 1               5

<210> SEQ ID NO 8
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Lys.  Artificial
      sequence is completely synthesized.

<400> SEQUENCE: 8

Xaa Pro Arg Arg Pro Tyr Ile Leu
 1               5
```

PATHOLOGICAL TISSUE DETECTION AND TREATMENT EMPLOYING TARGETED BENZOINDOLE OPTICAL AGENTS

RELATED APPLICATIONS

This application is a Continuation of co-pending U.S. patent application Ser. No. 10/847,257, filed May 17, 2004; a Continuation of co-pending U.S. patent application Ser. No. 10/847,256, filed May 17, 2004; and a Continuation of co-pending U.S. patent application Ser. No. 10/847,121, filed May 17, 2004, each of which are Divisions of U.S. patent application Ser. No. 09/978,725, filed Oct. 17, 2001, now U.S. Pat. No. 6,761,878, each of which is expressly incorporated by reference herein in its entirety, and was also filed as U.S. patent application Ser. No. 09/981,206, filed on Oct. 17, 2001, now abandoned.

FIELD OF THE INVENTION

This invention relates to novel dye-bioconjugates for use in diagnosis and therapy, particularly novel compositions of cyanine dye bioconjugates of bioactive molecules.

BACKGROUND

Cancer will continue to be a primary cause of death for the foreseeable future, but early detection of tumors would improve patient prognosis (R. T. Greenlee et al., Cancer statistics, 2000, CA Cancer J. Clin., 2000, 50, pp. 7-33). Despite significant advances in current methods for the diagnosis of cancer, physicians still rely on the presence of a palpable tumor mass. At this, however, the many benefits of early medical intervention may have been already compromised.

Photodiagnosis and/or phototherapy has a great potential to improve management of cancer patient (D. A. Benaron and D. K. Stevenson, Optical time-of-flight and absorbance imaging of biologic media, Science, 1993, 259, pp. 1463-1466; R. F. Potter (Series Editor), Medical optical tomography: functional imaging and monitoring, SPIE Optical Engineering Press, Bellingham, 1993; G. J. Tearney et al., In vivo endoscopic optical biopsy with optical coherence tomography, Science, 1997, 276, pp. 2037-2039; B. J. Tromberg et al., Non-invasive measurements of breast tissue optical properties using frequency-domain photon migration, Phil. Trans. Royal Society London B, 1997, 352, pp. 661-668; S. Fantini et al., Assessment of the size, position, and optical properties of breast tumors in vivo by non-invasive optical methods, Appl. Opt., 1998, 37, pp. 1982-1989; A. Pelegrin et al., Photoimmunodiagnosis with antibody-fluorescein conjugates: in vitro and in vivo preclinical studies, J. Cell Pharmacol., 1992, 3, pp. 141-145). These procedures use visible or near infrared light to induce the desired effect. Both optical detection and phototherapy have been demonstrated to be safe and effective in clinical settings and biomedical research (B. C. Wilson, Optical properties of tissues, Encyclopedia of Human Biology, 1991, 5, 587-597; Y-L. He et al., Measurement of blood volume using indocyanine green measured with pulse-spectrometry: Its reproducibility and reliability, Critical Care Medicine, 1998, 26, pp. 1446-1451; J. Caesar et al., The use of Indocyanine green in the measurement of hepatic blood flow and as a test of hepatic function, Clin. Sci., 1961, 21, pp. 43-57; R. B. Mujumdar et al., Cyanine dye labeling reagents: Sulfoindocyanine succinimidyl esters, Bioconjugate Chemistry, 1993, 4, pp. 105-111; U.S. Pat. No. 5,453,505; Eric Hohenschuh, et al., Light imaging contrast agents, WO 98/48846; Jonathan Turner, et al., Optical diagnostic agents for the diagnosis of neurodegenerative diseases by means of near infra-red radiation, WO 98/22146; Kai Licha, et al., In-vivo diagnostic process by near infrared radiation, WO 96/17628; Robert A. Snow, et al., Compounds, WO 98/48838].

Dyes are important to enhance signal detection and/or photosensitizing of tissues in optical imaging and phototherapy. Previous studies have shown that certain dyes can localize in tumors and serve as a powerful probe for the detection and treatment of small cancers (D. A. Bellnier et al., Murine pharmacokinetics and antitumor efficacy of the photodynamic sensitizer 2-[1-hexyloxyethyl]-2-devinyl pyropheophorbide-a, J. Photochem. Photobiol., 1993, 20, pp. 55-61; G. A. Wagnieres et al., In vivo fluorescence spectroscopy and imaging for oncological applications Photochem. Photobiol., 1998, 68, pp. 603-632; J. S. Reynolds et al., Imaging of spontaneous canine mammary tumors using fluorescent contrast agents, Photochem. Photobiol., 1999, 70, pp. 87-94). However, these dyes do not localize preferentially in malignant tissues.

Efforts have been made to improve the specificity of dyes to malignant tissues by conjugating dyes to large biomolecules (A. Pelegrin, et al., Photoimmunodiagnosis with antibody-fluorescein conjugates: in vitro and in vivo preclinical studies, J. Cell Pharmacol., 1992, 3, pp. 141-145; B. Ballou et al., Tumor labeling in vivo using cyanine-conjugated monoclonal antibodies, Cancer Immunol. Immunother., 1995, 41, pp. 257-263; R. Weissleder et al., In vivo imaging of tumors with protease-activated near-infrared fluorescent probes, Nature Biotech., 1999, 17, pp. 375-378; K. Licha et al., New contrast agents for optical imaging: Acid-cleavable conjugates of cyanine dyes with biomolecules, Proc. SPIE, 1999, 3600, pp. 29-35). Developing a dye that can combine the roles of tumor-seeking, diagnostic, and therapeutic functions has been very difficult for several reasons. The dyes currently in use localize in tumors by a non-specific mechanism that usually relies on the lipophilicity of the dye to penetrate the lipid membrane of the cell. These lipophilic dyes require several hours or days to clear from normal tissues, and low tumor-to-normal tissue ratios are usually encountered. Furthermore, combining photodynamic properties with fluorescence emission needed for the imaging of deep tissues requires a molecule that must compromise either the photosensitive effect of the dye or the fluorescence quantum yield. Photosensitivity of phototherapy agents relies on the transfer of energy from the excited state of the agent to surrounding molecules or tissues, while fluorescence emission demands that the excitation energy be emitted in the form of light (T. J. Dougherty et al., Photoradiation therapy II: Cure of animal tumors with hematoporphyrin and light, Journal of National Cancer Institute, 1978, 55, pp. 115-121). Therefore, compounds and compositions that have optimal tumor-targeting ability to provide a highly efficient photosensitive agent for treatment of tumors are needed. Such agents would exhibit enhanced specificity for tumors and would also have excellent photophysical properties for optical detection.

Each of the references previously disclosed is expressly incorporated by reference herein in its entirety.

SUMMARY

The invention is directed to a composition for a carbocyanine dye bioconjugate. The bioconjugate consists of three components: 1) a tumor specific agent, 2) a photosensitizer (phototherapy) agent, and 3) a photodiagnostic agent. The inventive bioconjugates use the multiple attachment points of carbocyanine dye structures to incorporate one or more receptor targeting and/or photosensitive groups in the same molecule. The composition may be used in various biomedical applications.

The invention is also directed to a method for performing a diagnostic and therapeutic procedure by administering an effective amount of the composition of the cyanine dye bioconjugate to an individual. The method may be used in various biomedical applications, such as imaging tumors, targeting tumors with anti-cancer drugs, and performing laser guided surgery.

DETAILED DESCRIPTION

The invention relates to novel compositions comprising cyanine dyes having a general formula 1

Formula 1 wherein $W_1$ and $W_2$ may be the same or different and are selected from the group consisting of —$CR^{10}R^{11}$, —O—, —$NR^{12}$, —S—, and —Se; $Y_1$, $Y_2$, $Z_1$, and $Z_2$ are independently selected from the group consisting of hydrogen, tumor-specific agents, phototherapy agents, —CONH-Bm, —NHCO-Bm, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_a$—N($R^{12}$)—$(CH_2)_b$—CONH-Bm, —$(CH_2)_a$—N($R^{12}$)—$(CH_2)_c$—NHCO-Bm, —$(CH_2)_a$—N($R^{12}$)—$(CH_2)_a$—N($R^{12}$)—$CH_2$—$(CH_2OCH_2)_b$—$CH_2$—CONH-Bm, —$(CH_2)_a$—N($R^{12}$)—$CH_2$—$(CH_2OCH_2)_b$—$CH_2$—NHCO-Bm, —$CH_2$—$(CH_2OCH_2)_b$—$CH_2$—N($R^{12}$)—$(CH_2)_a$—CONH-Bm, —$CH_2$—$(CH_2OCH_2)_b$—$CH_2$—N($R^{12}$)—$(CH_2)_a$—NHCO-Bm, —$CH_2$—$(CH_2OCH_2)_b$—$CH_2$—N($R^{12}$)—$CH_2$—$(CH_2OCH_2)_d$—CONH-Bm, —$CH_2$—$(CH_2OCH_2)_b$—$CH_2$—N($R^{12}$)—$CH_2$—$(CH_2OCH_2)_d$—NHCO-Bm, —CONH-Dm, —NHCO-Dm, —$(CH_2)_a$—CONH-Dm, —$CH_2$—$(CH_2OCH_2)_b$—$CH_2$—CONH-Dm, —$(CH_2)_a$—NHCO-Dm, —$CH_2$—$(CH_2OCH_2)_b$—$CH_2$—NHCO-Dm, —$(CH_2)_a$—N($R^{12}$)—$(CH_2)_b$—CONH-Dm, —$(CH_2)_a$—N($R^{12}$)—$(CH_2)_c$—NHCO-Dm, —$(CH_2)_a$—N($R^{12}$)—$CH_2$—$(CH_2OCH_2)_b$—$CH_2$—CONH-Dm, —$(CH_2)_a$—N($R^{12}$)—$CH_2$—$(CH_2OCH_2)_b$—$CH_2$—NHCO-Dm, —$CH_2$—$(CH_2OCH_2)_b$—$CH_2$—N($R^{12}$)—$(CH_2)_a$—CONH-Dm, —$CH_2$—$(CH_2OCH_2)_b$—$CH_2$—N($R^{12}$)—$(CH_2)_a$—NHCO-Dm, —$CH_2$—$(CH_2OCH_2)_b$—$CH_2$—N($R^{12}$)—$CH_2$—$(CH_2OCH_2)_d$—CONH-Dm, —$CH_2$—$(CH_2OCH_2)_b$—$CH_2$—N($R^{12}$)—$CH_2$—$(CH_2OCH_2)_d$—NHCO-Dm, —$(CH_2)_a$—$NR^{12}R^{13}$, and —$CH_2(CH_2OCH_2)_b$—$CH_2NR^{12}R^{13}$; $K_1$ and $K_2$ are independently selected from the group consisting of $C_1$-$C_{30}$ alkyl, $C_5$-$C_{30}$ aryl, $C_1$-$C_{30}$ alkoxyl, $C_1$-$C_{30}$ polyalkoxyalkyl, $C_1$-$C_{30}$ polyhydroxyalkyl, $C_5$-$C_{30}$ polyhydroxyaryl, $C_1$-$C_{30}$ aminoalkyl, saccharides, peptides, —$CH_2(CH_2OCH_2)_b$—$CH_2$—, —$(CH_2)_a$—CO—, —$(CH_2)_a$—CONH—, —$CH_2$—$(CH_2OCH_2)_b$—$CH_2$—CONH—, —$(CH_2)_a$—NHCO—, —$CH_2$—$(CH_2OCH_2)_b$—$CH_2$—NHCO—, —$(CH_2)_a$—O—, and —$CH_2$—$(CH_2OCH_2)_b$—CO—; $X_1$ and $X_2$ are single bonds, or are independently selected from the group consisting of nitrogen, saccharides, —$CR^{14}$—, —$CR^{14}R^{15}$, —$NR^{16}R^{17}$; $C_5$-$C_{30}$ aryl; Q is a single bond or is selected from the group consisting of —O—, —S—, —Se—, and —$NR^{18}$; a, and b, independently vary from 0 to 5; $R^1$ to $R^{13}$, and $R^{18}$ are independently selected from the group consisting of hydrogen, $C_1$-$C_{10}$ alkyl, $C_6$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, cyano, nitro, halogens, saccharides, peptides, —$CH_2(CH_2OCH_2)_b$—$CH_2$—OH, —$(CH_2)_a$—$CO_2H$, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_a$—OH and —$CH_2$—$(CH_2OCH_2)_b$—$CO_2H$; $R^{14}$ to $R^{17}$ are independently selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, saccharides, peptides, —$CH_2(CH_2OCH_2)_b$—$CH_2$—, —$(CH_2)_a$—CO—, —$(CH_2)_a$—CONH—, —$CH_2$—$(CH_2OCH_2)_b$—$CH_2$—CONH—, —$(CH_2)_a$—NHCO—, —$CH_2$—$(CH_2OCH_2)_b$—$CH_2$—NHCO—, —$(CH_2)_a$—O—, and —$CH_2$—$(CH_2OCH_2)_b$—CO—; Bm and Dm are independently selected from the group consisting of bioactive peptides, proteins, cells, antibodies, antibody fragments, saccharides, glycopeptides, peptidomimetics, drugs, drug mimics, hormones, metal chelating agents, radioactive or nonradioactive metal complexes, echogenic agents, photoactive molecules, and phototherapy agents (photosensitizers); a and c independently vary from 1 to 20; b and d independently vary from 1 to 100.

The invention also relates to the novel composition comprising carbocyanine dyes having a general formula 2

Formula 2 wherein $W_1$, $W_2$, $Y_1$, $Y_2$, $Z_1$, $Z_2$, $K_1$, $K_2$, Q, $X_1$, $X_2$, $a_1$, and $b_1$ are defined in the same manner as in Formula 1; and $R^{19}$ to $R^{31}$ are defined in the same manner as $R^1$ to $R^9$ in Formula 1.

The invention also relates to the novel composition comprising carbocyanine dyes having a general formula 3

Formula 3 wherein $A_1$ is a single or a double bond; $B_1$, $C_1$, and $D_1$ are independently selected from the group consisting of —O—, —S—, —Se—, —P—, —$CR^{10}R^{11}$—, —$CR^{11}$, alkyl, $NR^{12}$, and —C=O; $A_1$, $B_1$, $C_1$, and $D_1$ may together form a 6- to 12-membered carbocyclic ring or a 6- to 12-membered heterocyclic ring optionally containing one or more oxygen, nitrogen, or sulfur atoms; and $W_1$, $W_2$, $Y_1$, $Y_2$, $Z_1$, $Z_2$, $K_1$, $K_2$, $X_1$, $X_2$, $a_1$, $b_1$, and $R^1$ to $R^{12}$ are defined in the same manner as in Formula 1.

Figure 1A:
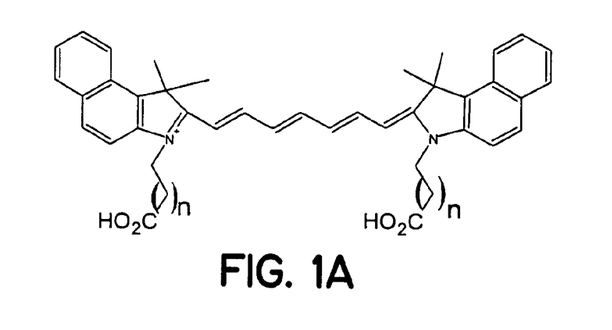
FIG. 1 shows representative structures of the inventive compounds.
Figure 1B:
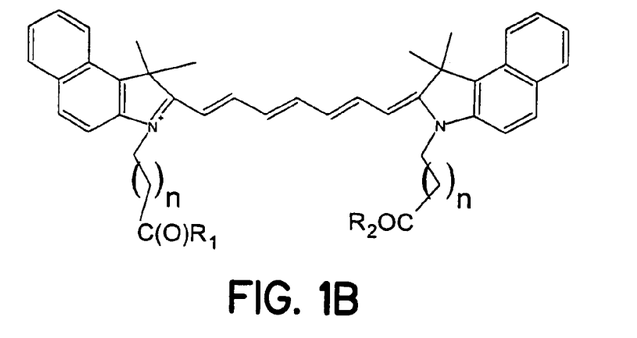
Figure 1C:
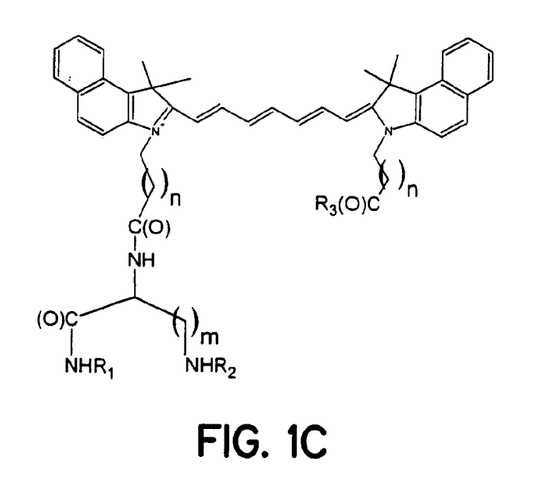

The present invention also relates to the novel composition comprising carbocyanine dyes having a general formula 4 which have high infrared molar absorbtivities (FIG. 1A-C). The invention provides each of these components, with their associated benefits, in one molecule for an optimum effect.

Such small dye biomolecule conjugates have several advantages over either nonspecific dyes or the conjugation of probes or photosensitive molecules to large biomolecules. These conjugates have enhanced localization and rapid visualization of tumors which is beneficial for both diagnosis and therapy. The agents are rapidly cleared from blood and non-target tissues so there is less concern for accumulation and for toxicity. A variety of high purity compounds may be easily synthesized for combinatorial screening of new targets, e.g., to identify receptors or targeting agents, and for the ability to affect the pharmacokinetics of the conjugates by minor structural changes.

The inventive compositions are useful for various biomedical applications. Examples of these applications include, but are not limited to: detecting, imaging, and treating of tumors; tomographic imaging of organs; monitoring of organ functions; performing coronary angiography, fluorescence endoscopy, laser guided surgery; and performing photoacoustic and sonofluorescent methods.

Specific embodiments to accomplish some of the aforementioned biomedical applications are given below. The inventive dyes are prepared according the methods well known in the art.

In two embodiments, the inventive bioconjugates have the formulas 1 or 2 where $W_1$ and $W_2$ may be the same or different and are selected from the group consisting of —$C(CH_3)_2$, Formula 4 wherein $A_1$, $B_1$, $C_1$, and $D_1$ are defined in the same manner as in Formula 3; $W_1$, $W_2$, $Y_1$, $Y_2$, $Z_1$, $Z_2$, $K_1$, $K_2$, $X_1$, $X_2$, $a_1$, and $b_1$ are defined in the same manner as in Formula 1; and $R^{19}$ to $R^{31}$ are defined in the same manner as $R^1$ to $R^9$ in Formula 1.

The inventive bioconjugates use the multiple attachment points of carbocyanine dye structures to incorporate one or more receptor targeting and/or photosensitive groups in the same molecule. More specifically, the inventive compositions consist of three components selected for their specific properties. One component, a tumor specific agent, is for targeting tumors. A second component, which may be a photosensitizer, is a phototherapy agent. A third component is a photodiagnostic agent.

Figure 1D:
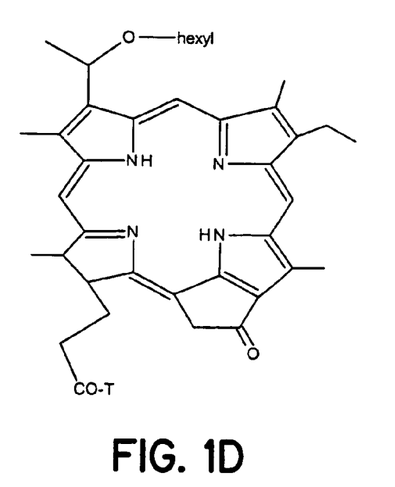
Figure 2A:
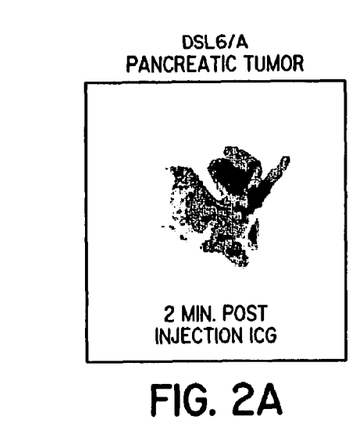
FIG. 2 shows images taken at two minutes and 30 minutes post injection of indocyanine green into rats with various tumors.
Figure 2B:
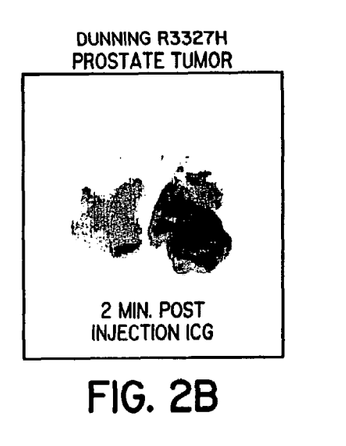
Figure 2C:
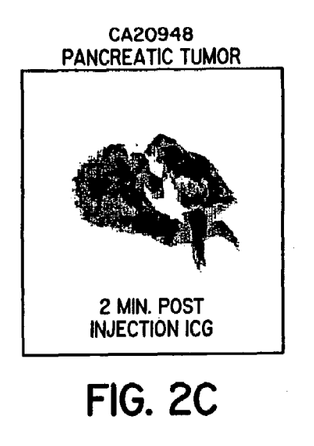
Figure 2D:
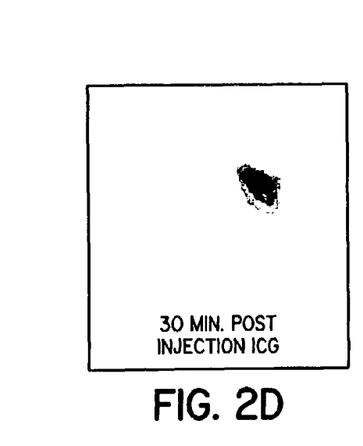
Figure 2E:
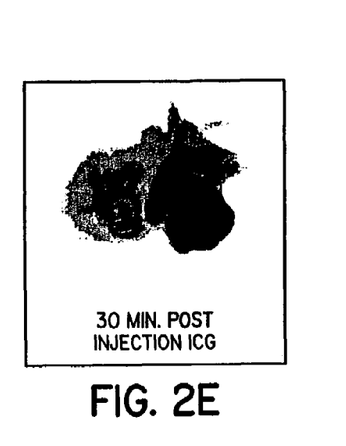
Figure 2F:
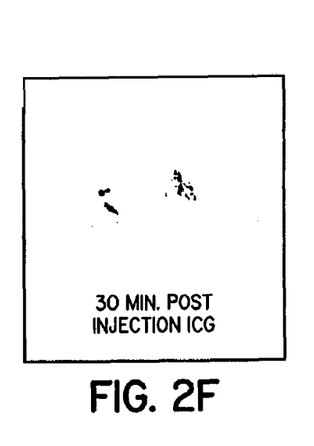

Examples of the tumor targeting agents are bioactive peptides such as octreotae and bombesin (7-14) which target overexpressed receptors in neuroendocrine tumors. An example of a phototherapy agent is 2-[1-hexyloxyethyl]-2-devinylpyro-pheophorbide-a (HPPH, FIG. 1D, T=OH). Examples of photodiagnostic agents are carbocyanine dyes —$C((CH_2)_aOH)CH_3$, —$C((CH_2)_aOH)_2$, —$C((CH_2)_aCO_2H)$ $CH_3$, —$C((CH_2)_aCO_2H)_2$, —$C((CH_2)_aNH_2)CH_3$, —$C((CH_2)_aNH_2)_2$, —$C((CH_2)_aNR^{12}R^{13})_2$, —$NR^{12}$, and —S—; $Y_1$ and $Y_2$ are selected from the group consisting of hydrogen, tumor-specific agents, —CONH-Bm, —NHCO-Bm, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_a$—$NR^{12}R^{13}$, and —$CH_2(CH_2OCH_2)_b$—$CH_2NR^{12}R^{13}$; $Z_1$ and $Z_2$ are independently selected from the group consisting of hydrogen, phototherapy agents, —CONH-Dm, —NHCO-Dm, —$(CH_2)_a$—CONH-Dm, —$CH_2$—$(CH_2OCH_2)_b$—$CH_2$—CONH-Dm, —$(CH_2)_a$—NHCO-Dm, —$CH_2$—$(CH_2OCH_2)_b$—$CH_2$—NHCO-Dm, —$(CH_2)_a$—$NR^{12}R^{13}$, and —$CH_2(CH_2OCH_2)_b$—$CH_2NR^{12}R^{13}$; $K_1$ and $K_2$ are independently selected from the group consisting of $C_1$-$C_{10}$ alkyl, $C_5$-$C_{20}$ aryl, $C_1$-$C_{20}$ alkoxyl, $C_1$-$C_{20}$ aminoalkyl, —$(CH_2)_a$—CO—, —$(CH_2)_a$—CONH, —$CH_2$—$(CH_2OCH_2)_b$—$CH_2$—CONH—, —$(CH_2)_a$—NHCO—, —$CH_2$—$(CH_2OCH_2)_b$—

$CH_2$—NHCO—, and —$CH_2$—$(CH_2OCH_2)_b$—CO—; $X_1$ and $X_2$ are single bonds, or are independently selected from the group consisting of nitrogen, —$CR^{14}$—, —$CR^{14}R^{15}$, and —$NR^{16}R^{17}$; Q is a single bond or is selected from the group consisting of —O—, —S—, and —$NR^{18}$; $a_1$ and $b_1$ independently vary from 0 to 3; Bm is selected from the group consisting of bioactive peptides containing 2 to 30 amino acid units, proteins, antibody fragments, mono- and oligosaccharides; Dm is selected from the group consisting of photosensitizers, photoactive molecules, and phototherapy agents; a and c independently vary from 1 to 20; and b and d independently vary from 1 to 100.

In two other embodiments, the bioconjugates according to the present invention have the formulas 3 or 4 wherein $W_1$ and $W_2$ may be the same or different and are selected from the group consisting of —$C(CH_3)_2$, —$C((CH_2)_aOH)CH_3$, —$C((CH_2)_aOH)_2$, —$C((CH_2)_aCO_2H)CH_3$, —$C((CH_2)_aCO_2H)_2$, —$C((CH_2)_aNH_2)CH_3$, —$C((CH_2)NH_2)_2$, —$C((CH_2)_aNR^{12}R^{13})_2$, —$NR^{12}$, and —S—; $Y_1$ and $Y_2$ are selected from the group consisting of hydrogen, tumor-specific agents, —CONH-Bm, —NHCO-Bm, —$(CH_2)_a$—CONH-Bm, —$CH_2$—$(CH_2OCH_2)_b$—$CH_2$—CONH-Bm, —$(CH_2)_a$—NHCO-Bm, —$CH_2$—$(CH_2OCH_2)_b$—$CH_2$—NHCO-Bm, —$(CH_2)_a$—$NR^{12}R^{13}$, and —$CH_2$ $(CH_2OCH_2)_b$—$CH_2NR^{12}R^{13}$; $Z_1$ and $Z_2$ are independently selected from the group consisting of hydrogen, phototherapy agents, —CONH-Dm, —NHCO-Dm, —$(CH_2)_a$—CONH-Dm, —$CH_2$—$(CH_2OCH_2)_b$—$CH_2$—CONH-Dm, —$(CH_2)_a$—NHCO-Dm, —$CH_2$—$(CH_2OCH_2)_b$—$CH_2$—NHCO-Dm, —$(CH_2)_a$—$NR^{12}R^{13}$, and —$CH_2$ $(CH_2OCH_2)_b$—$CH_2NR^{12}R^{13}$; $K_1$ and $K_2$ are independently selected from the group consisting of $C_1$-$C_{10}$ alkyl, $C_5$-$C_{20}$ aryl, $C_1$-$C_{20}$ alkoxyl, $C_1$-$C_{20}$ aminoalkyl, —$(CH_2)_a$—CO—, —$(CH_2)_a$—CONH, —$CH_2$—$(CH_2OCH_2)_b$—$CH_2$—CONH—, —$(CH_2)_a$—NHCO—, —$CH_2$—$(CH_2OCH_2)_b$—$CH_2$—NHCO—, and —$CH_2$—$(CH_2OCH_2)_b$—CO—; $X_1$ and $X_2$ are single bonds or are independently selected from the group consisting of nitrogen, —$CR^{14}$—, —$CR^{14}R^{15}$, and —$NR^{16}R^{17}$; $A_1$ is a single or a double bond; $B_1$, $C_1$, and $D_1$ are independently selected from the group consisting of —O—, —S—, —$CR^{11}$, alkyl, $NR^{12}$, and —C=O; $A_1$, $B_1$, $C_1$, and $D_1$ may together form a 6- to 12-membered carbocyclic ring or a 6- to 12-membered heterocyclic ring optionally containing one or more oxygen, nitrogen, or sulfur atoms; a, and b, independently vary from 0 to 3; Bm is selected from the group consisting of bioactive peptides containing 2 to 30 amino acid units, proteins, antibody fragments, mono- and oligosaccharides; bioactive peptides, protein, and oligosaccharide; Dm is selected from the group consisting of photosensitizers, photoactive molecules, and phototherapy agents; a and c independently vary from 1 to 20; and b and d independently vary from 1 to 100.

In one embodiment of the invention, the dye-biomolecule conjugates are useful for optical tomographic, endoscopic, photoacoustic and sonofluorescent applications for the detection and treatment of tumors and other abnormalities. These methods use light of wavelengths in the region of 300-1300 nm. For example, optical coherence tomography (OCT), also referred to as "optical biopsy," is an optical imaging technique that allows high resolution cross sectional imaging of tissue microstructure. OCT methods use wavelengths of about 1280 nm.

In various aspects of the invention, the dye-biomolecule conjugates are useful for localized therapy for the detection of the presence or absence of tumors and other pathologic tissues by monitoring the blood clearance profile of the conjugates, for laser assisted guided surgery (LAGS) for the detection and treatment of small micrometastases of tumors, e.g., somatostatin subtype 2 (SST-2) positive tumors, upon laproscopy, and for diagnosis of atherosclerotic plaques and blood clots.

In another embodiment, a therapeutic procedure comprises attaching a porphyrin or photodynamic therapy agent to a bioconjugate, and then administering light of an appropriate wavelength for detecting and treating an abnormality.

The compositions of the invention can be formulated for enteral or parenteral administration. These formulations contain an effective amount of the dye-biomolecule conjugate along with conventional pharmaceutical carriers and excipients appropriate for the type of administration contemplated. For example, parenteral formulations advantageously contain a sterile aqueous solution or suspension of the inventive conjugate, and may be injected directly, or may be mixed with a large volume parenteral composition or excipient for systemic administration as is known to one skilled in the art. These formulations may also contain pharmaceutically acceptable buffers and/or electrolytes such as sodium chloride.

Formulations for enteral administration may vary widely, as is well known in the art. In general, such formulations are aqueous solutions, suspensions or emulsions which contain an effective amount of a dye-biomolecule conjugate. Such enteral compositions may include buffers, surfactants, thixotropic agents, and the like. Compositions for oral administration may also contain flavoring agents and other ingredients for enhancing their organoleptic qualities.

The inventive compositions of the carbocyanine dye bioconjugates for diagnostic uses are administered in doses effective to achieve the desired effect. Such doses may vary widely, depending upon the particular conjugate employed, the organs or tissues which are the subject of the imaging procedure, the imaging equipment being used, and the like. The compositions may be administered either systemically, or locally to the organ or tissue to be imaged, and the patient is then subjected to diagnostic imaging and/or therapeutic procedures.

The present invention is further detailed in the following Examples, which are offered by way of illustration and are not intended to limit the scope of the invention in any manner.

EXAMPLE 1

Synthesis of Indocyaninebispropanoic Acid Dye
(FIG. 1A, n=1)

A mixture of 1,1,2-trimethyl-[1H]-benz[e]indole (9.1 g, 43.58 mmoles) and 3-bromopropanoic acid (10.0 g, 65.37 mmoles) in 1,2-dichlorobenzene (40 ml) was heated at 110° C. for 12 hours. The solution was cooled to ambient temperature. The red residue obtained was filtered and washed with acetonitrile:diethyl ether (1:1$^{v/v}$) mixture. The solid obtained was dried at ambient temperature under vacuum to give 10 g (64%) of light brown powder.

A portion of this solid (6.0 g; 16.56 mmoles), glutaconic aldehyde dianilide hydrochloride (Lancaster Synthesis, Windham, N.H.) (2.36 g, 8.28 mmoles), and sodium acetate trihydrate (2.93 g, 21.53 mmoles) in ethanol (150 ml) were refluxed for 90 minutes. After evaporating the solvent, 40 ml of a 2 N aqueous HCl was added to the residue. The mixture was centrifuged and the supernatant was decanted. This procedure was repeated until the supernatant became nearly colorless. About 5 ml of a water:acetonitrile (3:2$^{v/v}$) mixture was added to the solid residue and lyophilized to obtain 2 g of dark green flakes. The purity of the compound was established with ¹H-nuclear magnetic resonance (¹H-NMR) and liquid chromatography/mass spectrometry (LC/MS) as is known to one skilled in the art.

EXAMPLE 2

Synthesis of Indocyaninebishexanoic Acid Dye
(FIG. 1A, n=4)

A mixture of 1,1,2-trimethyl-[1H]-benz[e]indole (20 g, 95.6 mmoles) and 6-bromohexanoic acid (28.1 g, 144.1 mmoles) in 1,2-dichlorobenzene (250 ml) was heated at 110 C for 12 hours. The green solution was cooled to ambient temperature and the brown solid precipitate that formed was collected by filtration. After washing the solid with 1,2-dichlorobenzene and diethyl ether, the brown powder obtained (24 g, 64%) was dried under vacuum at ambient temperature. A portion of this solid (4.0 g; 9.8 mmoles) glutacoaldehyde dianil monohydrochloride (1.4 g, 5 mmoles) and sodium acetate trihydrate (1.8 g, 12.9 mmoles) in ethanol (80 ml) were refluxed for 1 hour. After evaporating the solvent, 20 ml of 2 N aqueous HCl was added to the residue. The mixture was centrifuged and the supernatant was decanted. This procedure was repeated until the supernatant became nearly colorless. About 5 ml of a water:acetonitrile ($3:2^{v/v}$) mixture was added to the solid residue and lyophilized to obtain about 2 g of dark green flakes. The purity of the compound was established with ¹H-NMR and LC/MS.

EXAMPLE 3

Synthesis of Peptides

Peptides of this invention were prepared by similar procedures with slight modifications in some cases.

Octreotate, an octapeptide, has the amino acid sequence D-Phe-Cys'-Tyr-D-Trp-Lys-Thr-Cys'-Thr (SEQ ID NO:1), wherein Cys' indicates the presence of an intramolecular disulfide bond between two cysteine amino acids. Octreotate was prepared by an automated fluorenylmethoxycarbonyl (Fmoc) solid phase peptide synthesis using a commercial peptide synthesizer from Applied Biosystems (Model 432A SYNERGY Peptide Synthesizer). The first peptide cartridge contained Wang resin pre-loaded with Fmoc-Thr on a 25-μmole scale. Subsequent cartridges contained Fmoc-protected amino acids with side chain protecting groups for the following amino acids: Cys(Acm), Thr(t-Bu), Lys(Boc), Trp (Boc) and Tyr(t-Bu). The amino acid cartridges were placed on the peptide synthesizer and the product was synthesized from the C- to the N-terminal position according to standard procedures. The coupling reaction was carried out with 75 μmoles of the protected amino acids in the presence of 2-(1H-benzotriazol-1-yl)-1,1,3,3-tetramethyluronium hexafluorophosphate (HBTU)/N-hydroxybenzotriazole (HOBt). The Fmoc protecting groups were removed with 20% piperidine in dimethylformamide.

After the synthesis was complete, the thiol group was cyclized with thallium trifluoroacetate and the product was cleaved from the solid support with a cleavage mixture containing trifluoroacetic acid:water:phenol:thioanisole (85:5:5:$5^{v/v}$) for 6 hours. The peptide was precipitated with t-butyl methyl ether and lyophilized with water:acetonitrile ($2:3^{v/v}$). The peptide was purified by HPLC and analyzed by LC/MS.

Octreotide, (D-Phe-Cys'-Tyr-D-Trp-Lys-Thr-Cys'-Thr-OH (SEQ ID NO:2)), wherein Cys' indicates the presence of an intramolecular disulfide bond between two cysteine amino acids) was prepared by the same procedure as that for octreotate with no modifications.

Bombesin analogs were prepared by the same procedure but cyclization with thallium trifluoroacetate was omitted. Side-chain deprotection and cleavage from the resin was carried out with 50 μl each of ethanedithiol, thioanisole and water, and 850 μl of trifluoroacetic acid. Two analogues were prepared: Gly-Ser-Gly-Gln-Trp-Ala-Val-Gly-His-Leu-Met-NH₂ (SEQ ID NO:3) and Gly-Asp-Gly-Gln-Trp-Ala-Val-Gly-His-Leu-Met-NH₂ (SEQ ID NO:4).

Cholecystokinin octapeptide analogs were prepared as described for Octreotate without the cyclization step. Three analogs were prepared: Asp-Tyr-Met-Gly-Trp-Met-Asp-Phe-NH₂ (SEQ ID NO:5); Asp-Tyr-Nle-Gly-Trp-Nle-Asp-Phe-NH₂ (SEQ ID NO:6); and D-Asp-Tyr-Nle-Gly-Trp-Nle-Asp-Phe-NH₂ (SEQ ID NO:7) wherein Nle is norleucine.

Neurotensin analog (D-Lys-Pro-Arg-Arg-Pro-Tyr-Ile-Leu (SEQ ID NO:8)) was prepared as described for Octreotate without the cyclization step.

EXAMPLE 4

Synthesis of Peptide-Dye Conjugates (FIG. 1B, n=1, $R_1$=Octreotate, $R_2$=$R_1$ or OH)

The method described below is for the synthesis of Octreotate-cyanine dye conjugates. Similar procedures were used for the synthesis of other peptide-dye conjugates.

Octreotate was prepared as described in Example 3, but the peptide was not cleaved from the solid support and the N-terminal Fmoc group of Phe was retained. The thiol group was cyclized with thallium trifluoroacetate and Phe was deprotected to liberate the free amine.

Bisethylcarboxymethylindocyanine dye (53 mg, 75 μmoles) was added to an activation reagent consisting of a mixture 0.2 M HBTU/HOBt in DMSO (375 μl), and 0.2 M diisopropylethylamine in DMSO (375 μl). The activation was complete in about 30 minutes. The resin-bound peptide (25 μmoles) was then added to the dye. The coupling reaction was carried out at ambient temperature for 3 hours. The mixture was filtered and the solid residue was washed with DMF, acetonitrile and THF. After drying the green residue, the peptide was cleaved from the resin, and the side chain protecting groups were removed with a mixture of trifluoroacetic acid:water:thioanisole:phenol (85:5:5:$5^{v/v}$). The resin was filtered and cold t-butyl methyl ether (MTBE) was used to precipitate the dye-peptide conjugate. The conjugate was dissolved in acetonitrile:water ($2:3^{v/v}$) and lyophilized.

The product was purified by HPLC to give the monooctreotatebisethylcarboxy-methylindocyanine dye (Cytate 1, 80%, n=1, $R_2$=OH) and the bisoctreotate-bisethylcarboxymethylindocyanine dye (Cytate 2, 20%, n=1, $R_1$=$R_2$).

The monooctreotate conjugate may be obtained almost exclusively (>95%) over the bis conjugate by reducing the reaction time to 2 hours. This, however, leads to an incomplete reaction, and the free octreotate must be carefully separated from the dye conjugate in order to avoid saturation of the receptors by the non-dye conjugated peptide.

EXAMPLE 5

Synthesis of Peptide-Dye Conjugates (FIG. 1B, n=4 $R_1$=octreotate, $R_2$=$R_1$ or OH)

Octreotate-bispentylcarboxymethylindocyanine dye was prepared as described in Example 4 with some modifications.

Bispentylcarboxymethyl-indocyanine dye (60 mg, 75 μmoles) was added to 400 μl activation reagent consisting of 0.2 M HBTU/HOBt and 0.2 M diisopropylethylamine in DMSO. The activation was complete in about 30 minutes and the resin-bound peptide (25 μmoles) was added to the dye. The reaction was carried out at ambient temperature for 3 hours. The mixture was filtered and the solid residue was washed with DMF, acetonitrile and THF. After drying the green residue, the peptide was cleaved from the resin and the side chain protecting groups were removed with a mixture of trifluoroacetic acid:water:thioanisole:phenol (85:5:5:5$^{v/v}$). The resin was filtered and cold t-butyl methyl ether (MTBE) was used to precipitate the dye-peptide conjugate. The conjugate was dissolved in acetonitrile:water (2:3$^{v/v}$) and lyophilized. The product was purified by HPLC to give octreotate-1,1,2-trimethyl-[1H]-benz[e]indole propanoic acid conjugate (10%), monooctreotate-bispentylcarboxymethylindocyanine dye (Cytate 3, 60%, n=4, $R_2$=OH) and bisoctreotate-bispentylcarboxymethylindocyanine dye (Cytate 4, 30%, n=4, $R_1$=$R_2$).

EXAMPLE 6

Synthesis of Peptide-Dye-Phototherapy Conjugates (FIG. 1B, n=4, $R_1$=Octreotate. $R_2$=HPPH) by Solid Phase Bispentylcarboxymethylindocyanine dye (cyhex, 60 mg, 75 □moles) in dichloromethane is reacted with cyanuric acid fluoride (21 mg, 150 mmoles) in the presence of pyridine (12 mg, 150 mmoles) for 30 minutes to produce an acid anhydride. One molar equivalent of 2-[1-hexyloxyethyl]-2-devinylpyropheophorbide-a (HPPH, FIG. 1D, T=—NHC$_2$H$_4$NH$_2$) is added to the anhydride to form the cyhex-HPPH conjugate with a free carboxylic acid group. This intermediate is added to an activation reagent consisting of a 0.2 M solution of HBTU/HOBt in DMSO (400 μl), and a 0.2 M solution of diisopropylethylamine in DMSO (400 μl). Activation of the carboxylic acid is complete in about 30 minutes. Resin-bound peptide (octreotate, 25 μmoles), prepared as described in Example 4, is added to the mixture. The reaction is carried out at ambient temperature for 8 hours. The mixture is filtered and the solid residue is washed with DMF, acetonitrile and THF. After drying the dark residue at ambient temperature, the peptide derivative is cleaved from the resin and the side chain protecting groups are removed with a mixture of trifluoroacetic acid:water:thioanisole:phenol (85:5:5:5$^{v/v}$). After filtering the resin, cold t-butyl methyl ether (MTBE) is used to precipitate the dye-peptide conjugate, which is then lyophilized in acetonitrile:water (2:3V/v).

EXAMPLE 7

Synthesis of Peptide-Dye-Phototherapy Conjugates (FIG. 1B, n=4, $R_1$=Octreotide, $R_2$=HPPH) by Solution Phase Derivatized HPPH ethylenediamine (FIG. 1D, T=—NHC$_2$H$_4$NH$_2$; 1.1 molar equivalents) and lysine(trityl)$^4$ octreotide (1.2 molar equivalents) were added to a solution of bis(pentafluorophenyl)ester of cyhex (1 molar equivalent) in DMF. After stirring the mixture for 8 hours at ambient temperature, cold t-butyl methyl ether was added to precipitate the peptide conjugate. The crude product was purified by high performance liquid chromatography (HPLC).

EXAMPLE 8

Synthesis of Peptide-Dye-Phototherapy Conjugates (FIG. 1C, n=4, $R_1$=K$^0$-Octreotate, $R_2$=HPPH, $R_3$=OH) by Solid Phase Orthogonally protected Fmoc-lysine(Mtt)$^0$ Octreotate was prepared on a solid support, as described in Examples 3 and 4. The Fmoc group of Fmoc-lysine(Mtt)$^0$ is removed from the solid support with 20% piperidine in DMF. HPPH (FIG. 1D, T=—OH), pre-activated with HBTU coupled to the free α-amino group of lysine.

EXAMPLE 9

Imaging of Tumor Cell Lines with Indocyanine Green

A non-invasive in vivo fluorescence imaging apparatus was employed to assess the efficacy of indocyanine green (ICG) in three different rat tumor cell lines of the inventive contrast agents developed for tumor detection in animal models. A LaserMax Inc. laser diode of nominal wavelength 780 nm and nominal power of 40 mW was used. The detector was a Princeton Instruments model RTE/CCD-1317-K/2 CCD camera with a Rodenstock 10 mm F2 lens (stock #542.032.002.20) attached. An 830 nm interference lens (CVI Laser Corp., part # F10-830-4-2) was mounted in front of the CCD input lens, such that only emitted fluorescent light from the contrast agent was imaged.

Three tumor cell lines, DSL 6/A (pancreatic), Dunning R3327-H (prostate), and CA20948 (pancreatic), which are rich in somatostatin (SST-2) receptors were induced into male Lewis rats by solid implant technique in the left flank area (Achilefu et al., *Invest. Radiology*, 2000, pp. 479-485). Palpable masses were detected nine days post implant.

The animals were anesthetized with xylazine:ketamine:acepromazine (1.5:1:0.5$^{v/v}$) at 0.8 ml/kg via intramuscular injection. The left flank was shaved to expose the tumor and surrounding surface area. A 21-gauge butterfly needle equipped with a stopcock connected to two syringes containing heparinized saline was placed into the tail vein of the rat. Patency of the vein was checked prior to administration of ICG. Each animal was administered a 0.5 ml dose of a 0.42 mg/ml solution of ICG in saline.

Two of the cell lines, DSL 6/A (pancreatic) and Dunning R3327-H (prostate) which are rich in somatostatin (SST-2) receptors indicated slow perfusion of the agent into the tumor over time. Images were taken at 2 minutes and 30 minutes post administration of ICG. Reasonable images were obtained for each. The third line, CA20948 (pancreatic), indicated only a slight and transient perfusion that was cleared after only 30 minutes post injection. This indicated that there was no non-specific localization of ICG into this tumor line compared to the other two lines which suggested a vastly different vascular architecture for this type of tumor (FIG. 2). The first two tumor lines (DSL 6/A and R3327-H) were not as highly vascularized as CA20948 which is also rich in somatostatin (SST-2) receptors. Consequently, the detection and retention of a dye in the CA20948 tumor model is an important index of receptor-mediated specificity.

EXAMPLE 10

Imaging of Rat Pancreatic Acinar Carcinoma (CA20948) with Cytate 1

The peptide, octreotate, is known to target somatostatin (SST-2) receptors. Therefore, the cyano-octreotates conjugate, Cytate 1, was prepared as described in Example 4. The pancreatic acinar carcinoma, CA20948, was induced into male Lewis rats as described in Example 9.

The animals were anesthetized with xylazine: ketamine: acepromazine (1.5:1.5:0.5$^{v/v}$) at 0.8 ml/kg via intramuscular injection. The left flank was shaved to expose the tumor and surrounding surface area. A 21-gauge butterfly needle equipped with a stopcock connected to two syringes containing heparinized saline was placed into the tail vein of the rat. Patency of the vein was checked prior to administration of Cytate 1 via the butterfly apparatus. Each animal was administered a 0.5 ml dose of a 1.0 mg/ml solution of Cytate 1 in 25%$^{(v/v)}$ dimethylsulfoxide/water.

Using the CCD camera apparatus, dye localization in the tumor was observed. Usually, an image of the animal was taken pre-injection of contrast agent, and the pre-injection image was subsequently subtracted (pixel by pixel) from the post-injection images to remove background. However, the background subtraction was not done if the animal had been removed from the sample area and was later returned for imaging several hours post injection. These images demonstrated the specificity of cytate 1 for the SST-2 receptors present in the CA20948 rat tumor model.

Figure 3A:
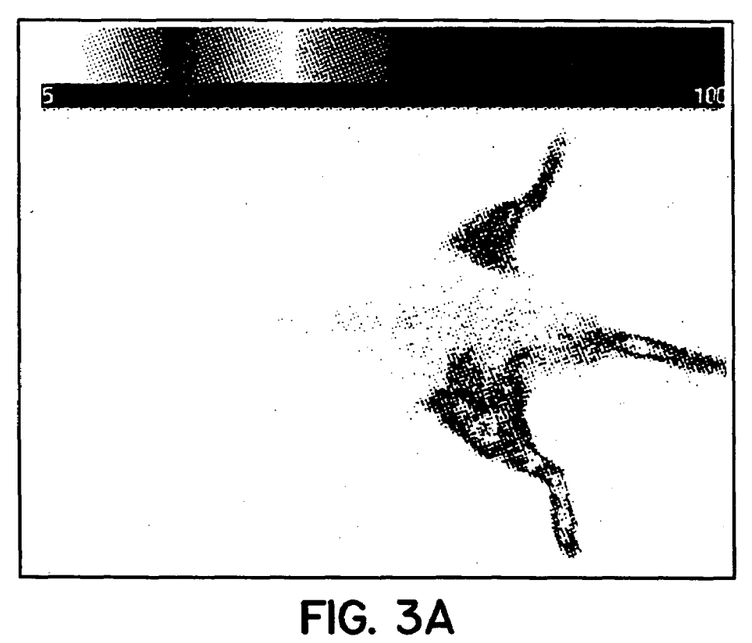
FIG. 3 shows fluorescent images of a CA20948 tumor bearing rat taken at one and 45 minutes post administration of cytate.
Figure 3B:
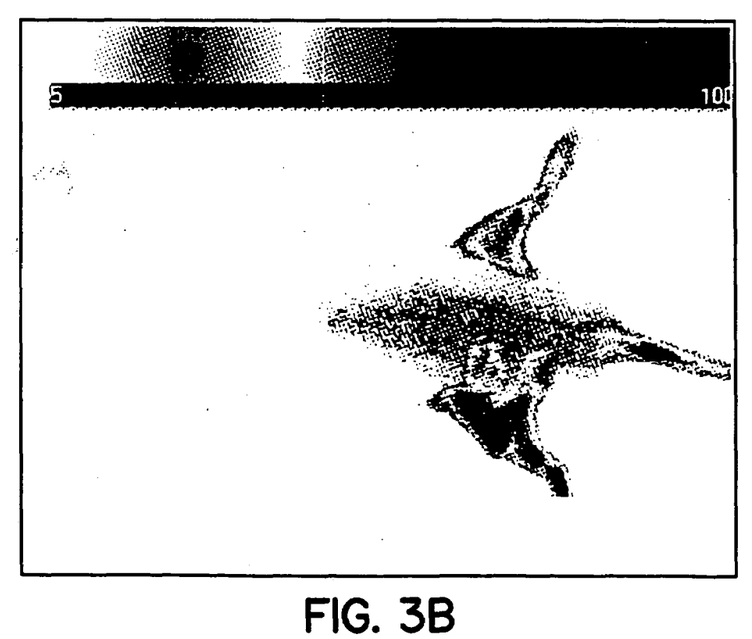
Figure 4:
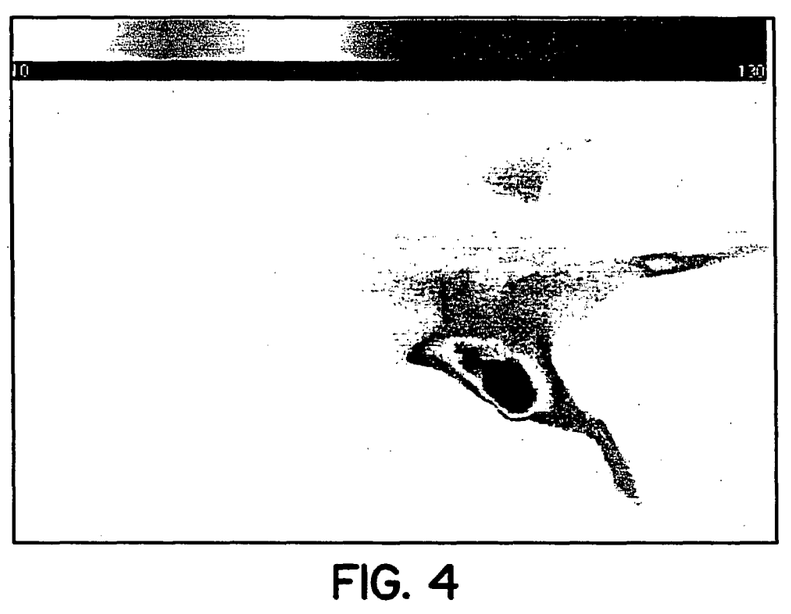
FIG. 4 is a fluorescent image of a CA20948 tumor bearing rat taken at 27 hours post administration of cytate.

At one minute post administration of cytate 1 the fluorescent image suggested the presence of the tumor in the left flank of the animal (FIG. 3a). At 45 minutes post administration, the image showed green and yellow areas in the left and right flanks and in the tail, however, there was a dark blue/blue green area in the left flank (FIG. 3b). AT 27 hours post administration of the conjugate, only the left flank showed a blue/blue green fluorescent area (FIG. 4).

Figure 5:
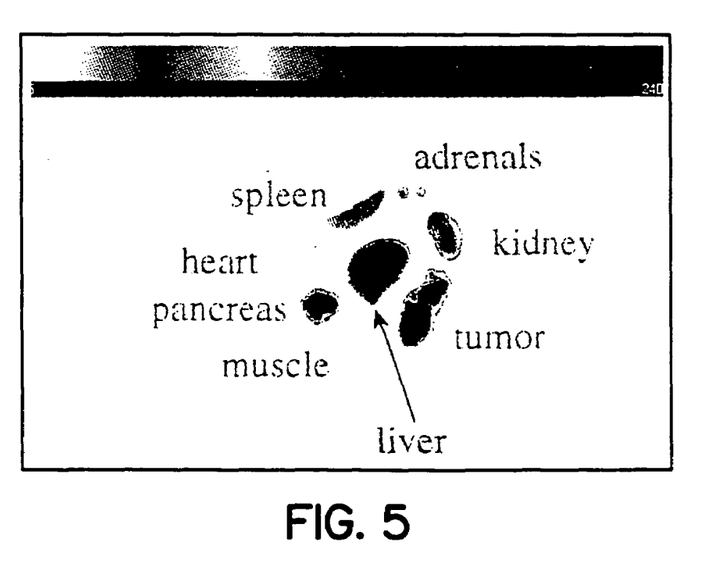
FIG. 5 shows fluorescent images of ex-vivo tissues and organs from a CA20948 tumor bearing rat at 27 hours post administration of cytate.

Individual organs were removed from the CA20948 rat which was injected with cytate 1 and were imaged. High uptake of the conjugate was observed in the pancreas, adrenal glands and tumor tissue. Significant lower uptake was observed in heart, muscle, spleen and liver (FIG. 5). These results correlated with results obtained using radiolabeled octreotate in the same rat model system (M. de Jong, et al. *Cancer Res.* 1998, 58, 437-441).

EXAMPLE 11

Imaging of Rat Pancreatic Acinar Carcinoma (AR42-J) with Bombesinate

The AR42-J cell line is derived from exocrine rat pancreatic acinar carcinoma. It can be grown in continuous culture or maintained in vivo in athymic nude mice, SCID mice, or in Lewis rats. This cell line is particularly attractive for in vitro receptor assays, as it is known to express a variety of hormone receptors including cholecystokinin (CCK), epidermal growth factor (EGF), pituitary adenylate cyclase activating peptide (PACAP), somatostatin (sst$_2$) and bombesin.

In this model, male Lewis rats were implanted with solid tumor material of the AR42-J cell line in a manner similar to that described in Example 9. Palpable masses were present 7 days post implant, and imaging studies were conducted on animals when the mass had achieved approximately 2 to 2.5 g (10-12 days post implant).

Figure 6:
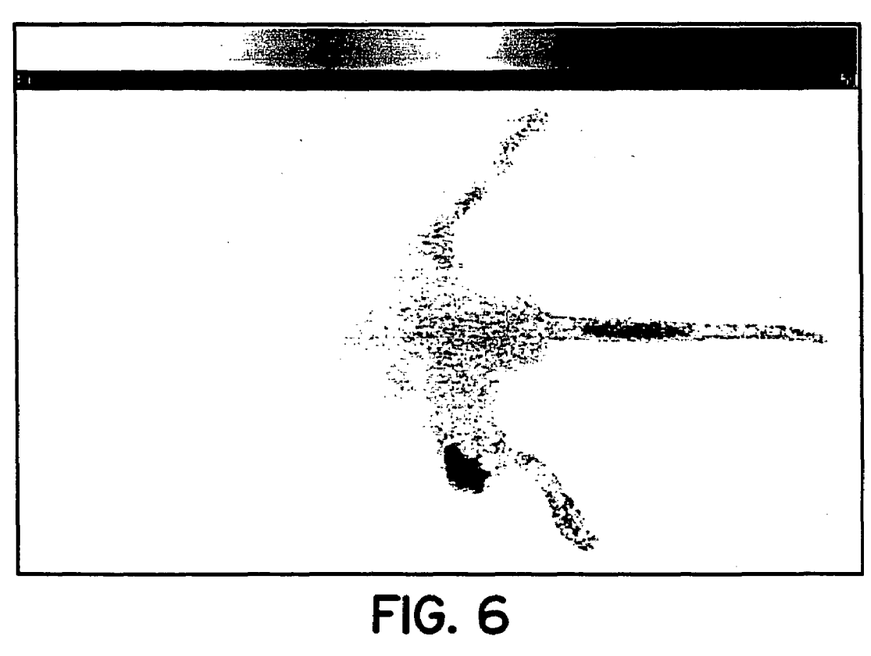
FIG. 6 is a fluorescent image of an AR42-J tumor bearing rat taken at 22 hours post administration of bombesinate.

FIG. 6 shows the image obtained with this tumor model at 22 hours post injection of bombesinate. Uptake of bombesinate was similar to that described in Example 10 for uptake of cytate 1 with specific localization of the bioconjugate in the tumor.

EXAMPLE 12

Imaging of Rat Pancreatic Acinar Carcinoma (CA20948) with Cytate 1 by Fluorescence Endoscopy Fluorescence endoscopy is suitable for tumors or other pathologic conditions of any cavity of the body. It is very sensitive and is used to detect small cancerous tissues, especially in the lungs and gastrointestinal (GI) system. Methods and procedures for fluorescence endoscopy are well-documented [Tajiri H., et al. Fluorescent diagnosis of experimental gastric cancer using a tumor-localizing photosensitizer. *Cancer Letters* (1997) 111, 215-220; Sackmann M., *Fluorescence diagnosis in GI endoscopy*, Endoscopy (2000) 32, 977-985, and references therein].

The fluorescence endoscope consists of a small optical fiber probe inserted through the working channel of a conventional endoscope. Some fibers within this probe deliver the excitation light at 780 nm and others detect the fluorescence from the injected optical probe at 830 nm. The fluorescence intensity is displayed on a monitor.

Briefly, the CA20948 rat pancreatic tumor cells which are over-expressing somatostatin receptor are injected into the submucosa of a Lewis rat. The tumor is allowed to grow for two weeks. The rat is then anesthetized with xylazine: ketamine: acepromazine (1.5:1.5:0.5$^{v/v}$) at 0.8 mL/kg via intramuscular injection. Cytate is injected in the tail vein of the rat and 60 minutes post-injection, the endoscope is inserted into the GI tract. Since cytate localizes in CA20948, the fluorescence intensity in the tumor is much higher than in the surrounding normal tissues. Thus, the relative position of the tumor is determined by observing the image on a computer screen.

EXAMPLE 13

Imaging of Rat Pancreatic Acinar Carcinoma (CA20948) with Cytate 1 by Photoacoustic Technique The photoacoustic imaging technique combines optical and acoustic imaging to allow better diagnosis of pathologic tissues. The preferred acoustic imaging method is ultrasonography where images are obtained by irradiating the animal with sound waves. The dual ultrasonography and optical tomography enables the imaging and localization of pathologic conditions (e.g., tumors) in deep tissues. To enhance the imaging, cytate is incorporated into ultrasound contrast material. Methods for the encapsulation of gases in biocompatible shells that are used as the contrast material are described in the literature [Mizushige K., et al., *Enhancement of ultrasound-accelerated thrombolysis by echo contrast agents: dependence on microbubble structure*, Ultrasound in Med. & Biol. (1999), 25, 1431-1437]. Briefly, perfluorocarbon gas (e.g., perfluorobutane) is bubbled into a mixture of normal saline propylene glycol:glycerol (7:1.5:1.5$^{v/v}$) containing 7 mg/ml of cytate dipalmitoylphosphatidylcholine:dipalmitoylphosphatidic acid, and dipalmitoylphosphatidyletha-nolamine-PEG 5,000 (1:7:1:1 mole %). The CA20948 tumor bearing Lewis rat is injected with 1 ml of the microbubbles and the agent is allowed to accumulate in the tumor. An optical image is obtained by exciting the near infrared dye at 780 nm and detecting the emitted light at 830 nm, as described in Examples 9-11. Ultrasonography is performed by irradiating the rat with sound waves in the localized tumor region and detecting the reflected sound as described in the literature [Peter J. A. Frinking, Ayache Bouakaz, Johan Kirkhorn, Folkert J. Ten Cate and Nico de Jong, *Ultrasound contrast imaging: current and new potential methods, Ultrasound in Medicine & Biology* (2000) 26, 965-975].

EXAMPLE 14

Photodynamic Therapy (PDT) and Localized Therapy of Rat Pancreatic Acinar Carcinoma (CA20948) with Cytate-PDT Agent Bioconjugates The method for photodynamic therapy is well documented in the literature [Rezzoug H., et al. *In Vivo Photodynamic Therapy with meso-Tetra (m-hydroxyphenyl)chlorin (mTHPC): Influence of Light Intensity and Optimization of Photodynamic Efficiency, Proc. SPIE* (1996), 2924, 181-186; Stranadko E., et al. *Photodynamic Therapy of Recurrent Cancer of Oral Cavity, an Alternative to Conventional Treatment, Proc.* SPIE (1996), 2924, 292-297]. A solution of the peptide-dye-phototherapy bioconjugate is prepared as described in Example 7 (5 μmol/mL of 15% DMSO in water, 0.5 mL) and is injected into the tail vein of the tumor-bearing rat. The rat is imaged 24 hours post injection as described in Examples 9-11 to localize the tumor. Once the tumor region is localized, the tumor is irradiated with light of 700 nm (which corresponds to the maximum absorption wavelength of HPPH, the component of the conjugate that effects PDT). The energy of radiation is 10 J/cm$^2$ at 160 mW/cm$^2$. The laser light is transmitted through a fiber optic, which is directed to the tumor. The rat is observed for 7 days and any decrease in tumor volume is noted. If the tumor is still present, a second dose of irradiation is repeated as described above until the tumor is no longer palpable.

For localized therapy, a diagnostic amount of cytate (0.5 mL/0.2 kg rat) is injected into the tail vein of the tumor-bearing rat and optical images are obtained as described in Examples 9-11. A solution of the peptide-dye-phototherapy bioconjugate is prepared as described in Example 7 (5 μmol/mL of 15% DMSO in water, 1.5 mL) and is injected directly into the tumor. The tumor is irradiated as described above.

EXAMPLE 15

Photodiagnosis with Atherosclerotic Plaques and Blood Clots

A solution of a peptide-dye-bioconjugate for targeting atherosclerotic plaques and associated blood clots is prepared as described in Example 7. The procedure for injecting the bioconjugate and subsequent localization and diagnosis of the plaques and clots is performed as described in Example 14.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A compound of the following formula wherein $W_1$ and $W_2$ are —$CR^{10}R^{11}$;

$Y_1$, $Y_2$, $Z_1$, and $Z_2$ are independently selected from hydrogen, tumor-specific agent, phototherapy agent, —CONH-Bm, —NHCO-Bm, —($CH_2$), —CONH-Bm, —$CH_2$—($CH_2OCH_2$)$_b$—$CH_2$CONH-Bm, —($CH_2$)$_a$—N HCO-Bm, —$CH_2$—$CH_2OCH_2$)$_b$—$CH_2$—NHCO-Bm, —($CH_2$)$_a$—N($R^{12}$)—($CH_2$)$_b$—CONH-Bm, —($CH_2$)a-N($R^{12}$)—($CH_2$)$_c$—NHCO-Bm, —($CH_2$)$_a$—N($R^{12}$)—$CH_2$—($CH_2OCH_2$)$_b$—$CH_2$—CONH-Bm, —($CH_2$)$_{a-N(R}$$^{12}$)—$CH_2$($CH_2OCH_2$)$_b$—$CH_2$—NHCO-Bm, —$CH_2$($CH_2OCH_2$)$_b$—$CH_2$—N($R^{12}$)—($CH_2$)$_b$—CONH-Bm, —$CH_2$—($CH_2$ $OCH_2$)$_b$—$CH_2$—N($R^{12}$)—($CH_2$)$_a$—NHCO-Bm, —$CH_2$($CH_2OCH_2$)$_b$—$CH_2$—N($R^{12}$)—$CH_2$—($CH_2OCH_2$)$_d$—CONH-Bm, —$CH_2$—($CH_2OCH_2$)$_b$—$CH_2$—N($R^{12}$)—$CH_2$—($CH_2OCH_2$)$_d$—NHCO-Bm, —CONH-Dm, —NHCO-Dm, —($CH_2$)$_a$—CONH-Dm, —$CH_2$—($CH_2OCH_2$)$_b$—$CH_2$—CONH-Dm, —($CH_2$)$_a$—NHCO-Dm, —$CH_2$—($CH_2OCH_2$)$_b$—$CH_2$—NHCO-Dm, —($CH_2$)$_a$—N($R^{12}$)—($CH_2$)$_b$—CONH-Dm, —($CH_2$)$_a$—N($R^{12}$)—($CH_2$)c-NHCO-Dm, —($CH_2$)$_a$—N($R^{12}$)—$CH_2$—($CH_2OCH_2$)$_b$—$CH_2$—CONH-Dm, —($CH_2$)$_a$—N($R^{12}$)—$CH_2$—($CH_2OCH_2$)$_b$—CHrNHCO-Dm, —$CH_2$—($CH_2OCH_2$)$_b$—$CH_2$—N($R^{12}$)—($CH_2$),—CONH-Dm, —$CH_2$—($CH_2OCH_2$)$_b$—$CH_2$—N($R^{12}$)—($CH_2$),—NHCO-Dm, —$CH_2$—($CH_2OCH_2$)b-$CH_2$—N($R^{12}$)—$CH_2$—($CH_2OCH_2$)$_d$—CONH-Dm, —$CH_2$—($CH_2OCH_2$)$_b$—$CH_2$—N($R^{12}$)—$CH_2$—($CH_2OCH_2$)$_d$—NHCO-Dm, —($CH_2$)$_a$—N $R^{12}R^{13}$, and —$CH_2$($CH_2OCH_2$)$_b$—$CH_2$N $R^{12}R^{13}$, wherein $Y_1$, $Y_2$, $Z_1$, and $Z_2$ are not simultaneously H;

$K_1$ and $K_2$ are independently selected from $C_1$-$C_{30}$ aryl, $C_5$-$C_{30}$ aryl, $C_1$-$C_{30}$ alkoxyl, $C_1$-$C_{30}$ polyalkoxyalkyl, $C_1$-$C_{30}$ polyhydroxyalkyl, $C_5$-$C_{30}$ polyhydroxyaryl, $C_1$-$C_{30}$ aminoalkyl, saccharide, peptide, —$CH_2$ ($CH_2OCH_2$)$_b$—$CH_2$-, —($CH_2$)$_a$—CO—, —($CH_2$)$_a$, —CONH—, —$CH_2$—($CH_2OCH_2$)$_b$—$CH_2$CONH—, —($CH_2$)$_a$—NHCO—, —$CH_2$—($CH_2OCH_2$)$_b$—$CH_2$—NHCO—,—($CH_2$)$_a$—O—, and —$CH_2$—($CH_2OCH_2$)$_b$—CO—;

$X_1$ and $X_2$ are independently selected from nitrogen and —$CR^{15}$;

A, is a single or a double bond;

$B_1$, $C_1$, and $D_1$ are independently selected from —O—, —S—, —Se—, —P—, —$CR^{10}R^{11}$, —$CR^{11}$, alkyl, $NR^{12}$, and —C=O;

$A_1$, $B_1$, $C_1$, and $D_1$ may together form a 6- to 12-membered carbocyclic ring or a 6- to 12-membered heterocyclic ring optionally containing one or more oxygen, nitrogen, or sulfur atom;

$a_1$ and $b_1$ independently vary from 0 to 5;

$R^1$ to $R^{13}$, and $R^{18}$ are independently selected from hydrogen, $C_1$-$C_{10}$ alkyl, $C_5$-$C_{20}$ aryl, $C_1$-$C_{10}$ alkoxyl, $C_1$-$C_{10}$ polyhydroxyalkyl, $C_1$-$C_{20}$ polyhydroxyalkyl, $C_5$-$C_{20}$) polyhydroxyaryl, $C_1$-$C_{10}$ aminoalkyl, cyano, nitro, halogen, saccharide, peptide, —$CH_2$($CH_2OCH_2$)$_b$—$CH_2$—OH, —($CH_2$)$_a$—$CO_2$H, —($CH_2$)$_a$—CONH- Bm, —CH$_2$—(CH$_2$OCH$_2$)$_b$—CH$_2$—CONH-Bm, —(CH$_2$)$_a$—NHCO-Bm, —CH$_2$—(CH$_2$OCH$_2$)$_b$—CH$_2$—NHCO-Bm, —(CH$_2$)$_a$—OH and —CH$_2$—(CH$_2$OCH$_2$)$_b$—CO$_2$H;

R$^{15}$ to R$^{17}$ are independently selected from hydrogen, C$_1$-C$_{10}$ alkyl, C$_5$-C$_{20}$ aryl, C$_1$-C$_{10}$ alkoxyl, C$_1$-C$_{10}$ polyalkoxyalkyt, C$_1$-C$_{20}$ polyhydroxyalkyl, C$_5$-C$_{20}$ polyhydroxyaryl, C$_1$-C$_{10}$ aminoalkyl, saccharide, peptide, —CH$_2$(CH$_2$OCH$_2$)$_b$—CH$_2$—, —(CH$_2$)a-CO—, —(CH$_2$)$_a$—CONH—, —CH$_2$—(CH$_2$OCH$_2$)$_b$—CH$_a$—CONH—, —(CH$_2$)$_a$—NHCO—, —CH$_2$—(CH$_2$OCH$_2$)$_b$—CH$_2$—NHCO—, —(CH$_2$)$_a$—O—, and —CH$_2$—(CH$_2$OCH$_2$)$_b$—CO—;

Bm and Dm are independently selected from bioactive peptide, protein, cell, antibody, antibody fragment, saccharide, glycopeptide, peptidomimetic, drug, drug mimic, hormone, metal chelating agent, radioactive or nonradioactive metal complex, echogenic agent, photoactive molecule, and phototherapy agent;

a and c independently vary from 1 to 20; and b and d independently vary from 1 to 100.

2. The compound of claim 1, wherein K$_1$ and K$_2$ are independently selected from C$_1$-C$_{30}$ alkyl, C$_5$-C$_{30}$ aryl, —CH$_2$(CH$_2$OCH$_2$)$_b$—CH$_2$, —(CH$_2$)$_a$—CO—, —(CH$_2$)$_a$—CONH, and —(CH$_2$)$_a$—O—.

3. A method of performing a diagnostic procedure to detect or image a tumor or performing a therapeutic procedure on a tumor or monitoring organ function, the method comprising:

administering to an individual an effective amount of a compound of claim 1; and performing the diagnostic or therapeutic procedure or monitoring organ function.

4. The method of claim 3, wherein the procedure utilizes light of wavelength in the region of 300-1300 nm.

5. The method of claim 3, wherein the procedure comprises optical tomography.

6. The method of claim 3, wherein the procedure comprises fluorescence endoscopy.

7. The method of claim 3, wherein the procedure is selected from the group consisting of absorption, light scattering, photoacoustic and sonofluoresence technique.

8. The method of claim 3, wherein the procedure is for diagnosing and treating atherosclerotic plaques and blood clots.

9. The method of claim 3, wherein the procedure comprises administering localized therapy.

10. The method of claim 3, wherein the procedure comprises photodynamic therapy.

11. The method of claim 3, wherein the procedure comprises laser assisted guided surgery (LAGS) for the detection and treatment of micrometastases.

* * * * *